United States Patent
Malatesta et al.

(10) Patent No.: US 12,016,847 B2
(45) Date of Patent: Jun. 25, 2024

(54) METHODS OF TREATING PROSTATE CANCER

(71) Applicant: Bristol-Myers Squibb Company, Princeton, NJ (US)

(72) Inventors: Martina Malatesta, San Francisco, CA (US); Ellen Hope Filvaroff, San Francisco, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 17/653,717

(22) Filed: Mar. 7, 2022

(65) Prior Publication Data

US 2022/0296574 A1 Sep. 22, 2022

Related U.S. Application Data

(60) Provisional application No. 63/160,319, filed on Mar. 12, 2021.

(51) Int. Cl.
A61K 31/437 (2006.01)
A61P 35/00 (2006.01)

(52) U.S. Cl.
CPC ............ *A61K 31/437* (2013.01); *A61P 35/00* (2018.01)

(58) Field of Classification Search
CPC ......... A61K 31/437; A61P 35/00; A61P 35/04
USPC ...................................................... 514/292
See application file for complete search history.

(56) References Cited

U.S. PATENT DOCUMENTS 9,458,156 B2 * 10/2016 Norris ..................... A61K 45/06
2016/0176864 A1 6/2016 Norris et al.

FOREIGN PATENT DOCUMENTS

| WO | 2010080429 A1 | 7/2010 |
|---|---|---|
| WO | 2012145173 A1 | 10/2012 |
| WO | 2013046635 A1 | 4/2013 |
| WO | 2014086739 A1 | 6/2014 |
| WO | 2014134232 A1 | 9/2014 |
| WO | 2014134267 A1 | 9/2014 |
| WO | 2014164596 A1 | 10/2014 |
| WO | 2019080941 A1 | 5/2019 |
| WO | 2021175432 A1 | 9/2021 |

OTHER PUBLICATIONS

Wyce et al: "Inhibition of BET bromodomain proteins as a therapeutic approach in prostate cancer.", Oncotarget, vol. 4, No. 12, Dec. 26, 2013, pp. 2419-2429, XP055408608.
Conway, S., ACS Med. Chem. Lett.; vol. 3 pp. 691-694 (2012).
Gorlitzer, K. et al., Die Pharmazie, Govi Verlag Pharmazeutischer Verlag GMBH, vol. 55 No. 4, pp. 273-281 (2000).
Hewings et al., J. Med. Chem., vol. 55, pp. 9393-9413 (2012).
Hilton J et al: "Initial results from a phase I/IIa trial evaluatingbrBMS-986158, an inhibitor of the bromodomain and extra-terminal (BET) proteins, in patients (pts) with advanced cancer", Annals of Oncology, Oct. 2018, page viiil 34, XP055931363.
Welti et al: "Targeting Bromodomain and Extra-Terminal (BET) Family Proteins in Castration-Resistant Prostate Cancer (CRPC)", Clinical Cancer Research, vol. 24, No. 13, Mar. 19, 2018, pages 3149-3162, XP055922706.
Yin Mingzhu et al: "Potent BRD4 inhibitor suppresses cancer cell-macrophage interaction", Nature Communications,brvol. 11, No. 1, Apr. 14, 2020, XP055931388.
Gavai, A., et al. "Discovery and Preclinical Pharmacology of an Oral Bromodomain and Extra-Terminal (BET) Inhibitor Using Scaffold-Hopping and Structure-Guided Drug Design" J. Med. Chem vol. 64, p. 14247-14265 (2021).

* cited by examiner

*Primary Examiner* — Charanjit Aulakh
(74) *Attorney, Agent, or Firm* — Elliott Korsen (57) ABSTRACT

The present application relates generally to methods for treating prostate cancer with substituted tricyclic derivative is 2-[3-(1,4-dimethyl-1H-1,2,3-triazol-5-yl)-5-[(S)-(oxan-4-yl)(phenyl)methyl]-5H-pyrido[3,2-b]indol-7-yl]propan-2-ol as a bromodomain inhibitor, or the pharmaceutically acceptable salt thereof.

17 Claims, 8 Drawing Sheets

METHODS OF TREATING PROSTATE CANCER

CROSS REFERENCE TO RELATED APPLICATIONS

This application is entitled to priority pursuant to 35 U.S.C. § 119(e) to U.S. provisional patent application No. 63/160,319, filed Mar. 12, 2021, which is incorporated herein in its entirety.

FIELD

The present application relates generally to compositions and methods for treating prostate cancer with a substituted heterocyclic derivative compound, or pharmaceutically acceptable salt thereof, as a bromodomain inhibitor.

BACKGROUND

Prostate cancer is the second leading cause of cancer-related death and the most commonly diagnosed cancer in men. Prostate cancer tumors are composed primarily of prostate luminal epithelial cells. Differentiation of prostate luminal epithelial cells is controlled in part by Androgen receptor (AR) driven expression of prostate-specific markers. AR are steroid receptors that function as transcription factors and control survival of the cells through mechanisms that remain unclear. Depletion of androgens causes death of normal prostate luminal epithelial cells, which demonstrates the critical role of the AR pathway in their survival. Cancerous prostate cells continue to express AR and their survival also depends on the presence of androgens, which makes androgen deprivation the therapy of choice for patients with advanced prostate cancers. First-line treatments for prostate cancer aim to reduce circulating androgen levels through the use of androgen deprivation therapies (ADT). While ADT is initially effective at reducing prostate cancer growth, after two to three years of treatment the majority of patients progress to castration-resistant prostate cancer (CRPC) and tumor growth will proceed even in the presence of castration levels of androgen. At this point of disease progression, the number of therapeutic options becomes very limited.

Thus, there remains a need for more effective treatments for prostate cancer, and this disclosure satisfies this need.

SUMMARY

The present application relates generally to compositions and methods for treating prostate cancer. The methods comprise administering a therapeutically effective amount of a bromodomain inhibitor compound (Compound A) having the structure, or a pharmaceutically acceptable salt thereof:

Compound A

The aspects and embodiments of the present disclosure provide for methods and pharmaceutical compositions for treating subjects with prostate cancer, such as castration resistant prostate cancer (CPRC), neuroendocrine prostate cancer (NEPC), and anti-androgen resistant prostate cancer.

Provided in one aspect is a method of treating prostate cancer in a subject in need thereof comprising administering to the subject a therapeutically effective amount of Compound A having the structure, Compound A or a pharmaceutically acceptable salt thereof; and wherein the prostate cancer is castration resistant prostate cancer (CPRC), neuroendocrine prostate cancer (NEPC), anti-androgen resistant prostate cancer, or any combination thereof.

In some embodiments, the prostate cancer is metastatic. In some embodiments, the prostate cancer to be treated is in an advanced stage. In some embodiments, the prostate cancer to be treated has metastasized to regions of the subject's body other than the prostate gland. In some embodiments, the prostate cancer to be treated has re-occurred in the subject following a significant period of remission. In some embodiments, the prostate cancer is castration resistant prostate cancer (CPRC). In some embodiments, the castration resistant prostate cancer (CPRC) is an androgen receptor (AR) independent disease characterized by neuroendocrine phenotype with a low or absent AR expression. In some embodiments, the prostate cancer is neuroendocrine prostate cancer (NEPC).

In some embodiments, the method results in substantially inducing cell cycle arrest of the prostate cancer. In some embodiments, "substantially" is defined as at least about 50%, at least about 55%, at least about 60%, at least about 65%, at least about 70%, at least about 75%, at least about 80%, at least about 85%, at least about 90%, at least about 95%, or at least about 100% cell cycle arrest of the prostate cancer. In some embodiments, the method results in completely inducing cell cycle arrest of the prostate cancer.

In some embodiments, the method induces apoptosis of androgen independent cancer cells. In some embodiments, the method results in inducing about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100% apoptosis of the androgen independent cancer cells.

In some embodiments, (a) the method results in at least about 70% reduction of cancer cell proliferation; (b) the method results in from about 70% to about 99% reduction of cancer cell proliferation; (c) the method results in at least about 80% reduction of cancer cell proliferation; (d) the method results in from about 80% to about 99% reduction of cancer cell proliferation; and/or (e) the method results in about 70%, about 75%, about 80%, about 85%, about 90%, about 95%, or about 99% reduction of cancer cell proliferation.

In some embodiments, (a) the method results in at least about 40% reduction of tumor size; (b) the method results in from about 40% to about 99% reduction of tumor size; and/or (c) the method results in about 20%, about 25%, about 30%, about 35%, about 40%, about 45%, about 50%, about 55%, about 60%, about 65%, about 70%, about 75%, about 80%, about 85%, about 90%, about 95%, or about 99% reduction of tumor size.

In some embodiments, the compound, or a pharmaceutically acceptable salt thereof, is adapted for oral administration. In some embodiments, the compound, or a pharmaceutically acceptable salt thereof, is in the form of a tablet, pill, sachet, or capsule of hard of soft gelatin.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

DETAILED DESCRIPTION

I. Overview

The present invention is directed to methods of treating prostate cancer with a therapeutically effective amount of a bromodomain inhibitor having a structure of Formula (I), or a pharmaceutically acceptable salt thereof. In particular, the prostate cancer is castration resistant prostate cancer (CPRC), neuroendocrine prostate cancer (NEPC), anti-androgen resistant prostate cancer, or any combination thereof.

This disclosure recognizes that in any of the embodiments described herein, the bromodomain inhibitor is present in an amount to substantially and/or completely induce cell cycle arrest of the prostate cancer cells and induce cell death in prostate carcinoma and neuroendocrine prostate cancer cells. The disclosure also encompasses methods whereby metastasis of the prostate cancer is prevented and/or delayed. In another aspect, the disclosure encompasses methods whereby prostate cancer cell growth arrest is observed after a short period of administration, e.g., less than about 1 month. In other aspects, prostate cancer cell growth arrest is observed in less than about 20, less than about 15, less than about 14, less than about 13, less than about 12, less than about 11, less than about 10, less than about 9, less than about 8, less than about 7, less than about 6, less than about 5, less than about 4, or less than about 3 days. The percentage of prostate cancer cell growth arrest observed after any of these time periods can be, for example, about 100%, about 95%, about 90%, about 85%, about 80%, about 75%, about 70%, about 65%, about 60%, about 55%, about 50%, about 45%, about 40%, about 35%, about 30%, about 25%, or about 20%.

In particular, Example 1 details the ability of Bromo and Extra-Terminal domain inhibitor (BETi) Compound A (is 2-[3-(1,4-dimethyl-1H-1,2,3-triazol-5-yl)-5-[(S)-(oxan-4-yl)(phenyl)methyl]-5H-pyrido[3,2-b]indol-7-yl]propan-2-ol) to completely arrest cell proliferation and induce cell death in prostate carcinoma and neuroendocrine prostate cancer cells. The experiments utilized multiple clinically acceptable cell models, including (i) VCaP cells, which exhibit characteristics of clinical prostate carcinoma including expression of Prostate-Specific Antigen (PSA) and androgen receptor (AR); (ii) LNCaP cells established from a metastatic lesion of human prostatic adenocarcinoma; (iii) 22Rv1 cells expressing the AR splice variant AR-V7 which mediates resistance to AR antagonist like Enzalutamide (iv) DU145 cells and (v) PC3 cells, which are both widely accepted NEPC cell models.

Figure 1:
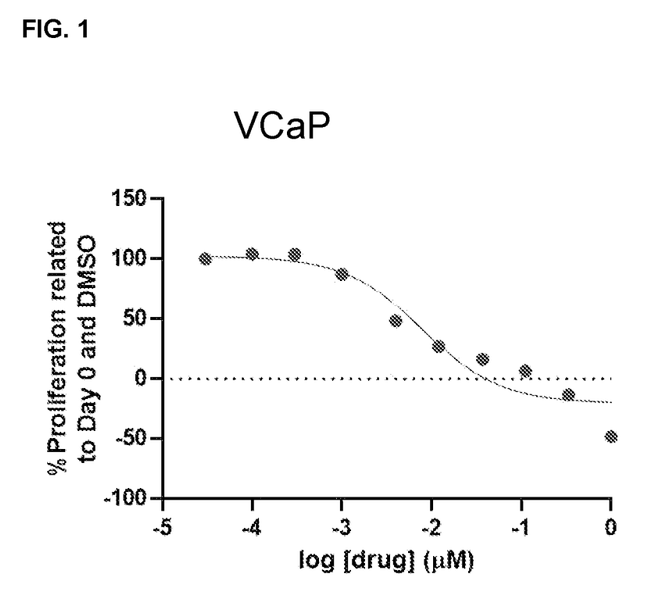
FIG. 1 shows VCaP cells treated with indicated concentrations of Compound A for 3 days. Proliferation was measured both at Day 0 and at Day 3, and percent of growth was determined using Luciferase assay.

Specifically, VCaP cells which exhibit characteristics of clinical prostate carcinoma including expression of PSA and AR, are used as a model to study prostate cancer progression and metastasis. To test the role of BET inhibition in prostate cancer, VCaP cells were treated with BETi Compound A. As visually shown in FIG. 1 which graphically shows the percent of VCaP cell growth related to Day 0 and DMSO (Y axis) versus the amount of Compound A (X axis), Compound A provided complete (100%) growth arrest for VCaP proliferation at 0.1 uM of Compound A. Moreover, Compound A exhibited cytotoxic effects at the highest concentration (FIG. 1).

Figure 2:
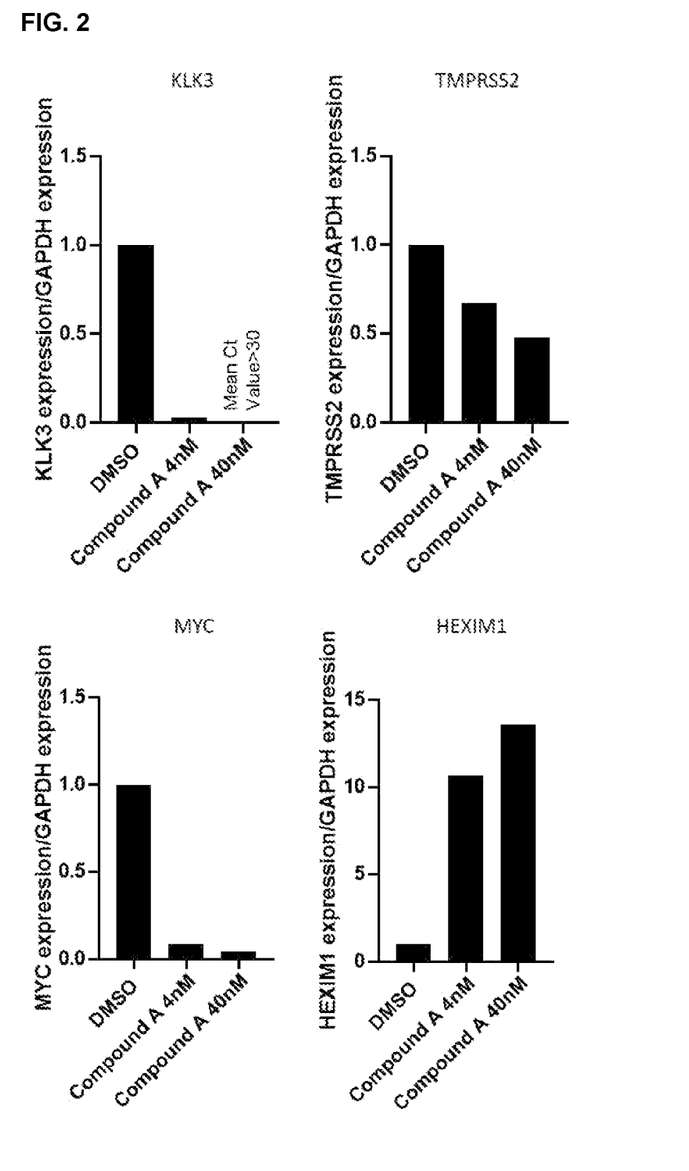
FIG. 2 shows VCaP cells treated with the indicated concentrations of Compound A for 48 h. KLK3, TMPRSS2, MYC and HEXIM1 genes expression was determined by qPCR.

Moreover, BET proteins regulate AR signaling through modulation of AR target genes. To test if BETi modulates AR target genes VCaP cells were treated with Compound A and gene expression was measured. Two AR target genes Kallikrein Related Peptidase 3 (KLK3) and Transmembrane Serine Protease 2 (TMPRSS2) were both downregulated after treatment with Compound A. When cells were treated with 4 nM of Compound A 96.9% of downregulation of KLK3 compared to DMSO was observed, while 99.4% downregulation of KLK3 compared to DMSO was measured in cells treated with 40 nM of Compound A (FIG. 2 top). Reduction of expression was also observed for TMPRSS2 with 32.8% and 51.9% of downregulation when 4 nM or 40 nM of Compound A were respectively administered to cells (FIG. 2 top). BET target genes such as MYC and Hexamethylene Bis-Acetamide-Inducible Protein 1 (HEXIM1) were also modulated by Compound A. In cells treated with 4 nM of Compound A 91.4% of reduction in MYC expression was observed, while in cells treated with 40 nM of Compound A 95.7% of MYC downregulation was measured. HEXIM1 was 968.0% and 1257.5% upregulated compared to DMSO when either 4 nM or 40 nM of Compound A was administered to VCaP cells (FIG. 2 bottom).

Figure 3:
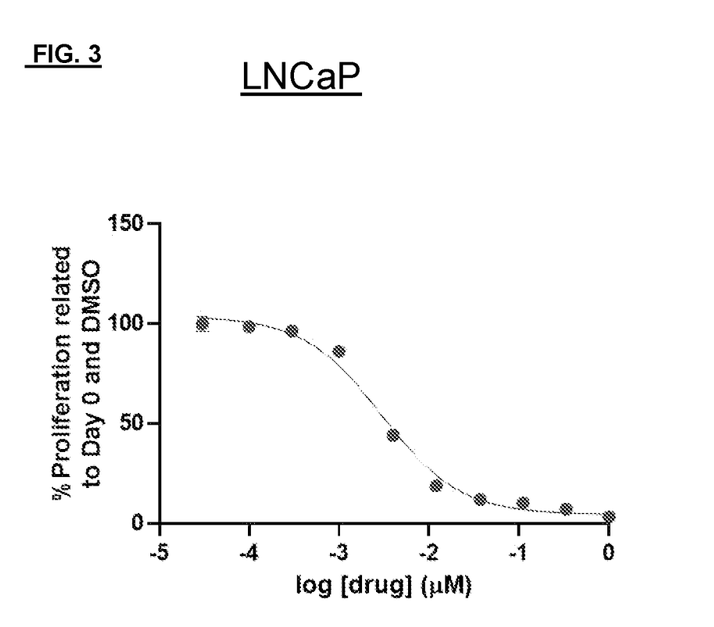
FIG. 3 shows LNCaP cells treated with indicated concentrations of Compound A for 3 days. Proliferation was measured both at Day 0 and at Day 3, and percent of growth was determined using Luciferase assay.

In addition, to further corroborate a role of BETi in prostate cancer LNCaP cells were treated with BETi Compound A. Treatment with Compound A provided complete (100%) growth arrest after only 3 days of treatment (FIG. 3). FIG. 3 graphically shows the percent of LNCaP cell growth related to Day 0 and DMSO (Y axis) versus the amount of Compound A (X axis). These results showed a 100% reduction of cell growth in both VCaP and LNCaP cells.

Figure 4:
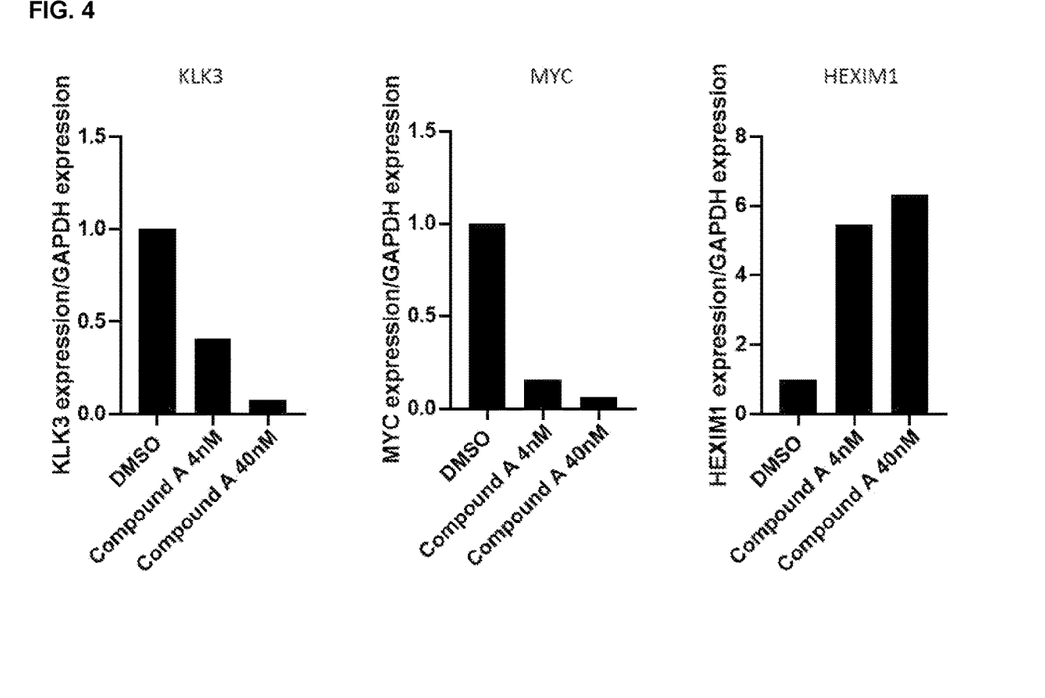
FIG. 4 shows LNCaP cells treated with indicated concentrations of Compound A for 48 hours. KLK3, MYC and HEXIM1 genes expression have been determined by qPCR.

Moreover, AR signaling was monitored in LNCaP cells after treatment with Compound A and a downregulation of KLK3 was observed with 58.8% and 92.0% of downregulation when 4 nM or 40 nM were respectively administered to the cells (FIG. 4). BETi target genes were also modulated. A downregulation of 84.1% of MYC was observed when 4 nM of Compound A was administered to the cells and 93.6% of downregulation was measured when 40 nM of Compound A was given to LNCaP cells. Finally, an upregulation of 446.8% and 533.3% of HEXIM1 was measured when cells were treated with respectively 4 nM and 40 nM of Compound A (FIG. 4)

Figure 5:
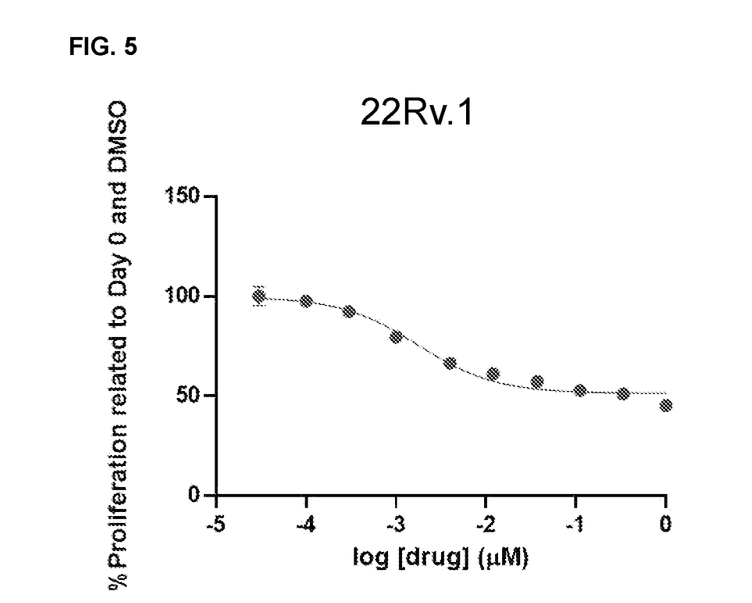
FIG. 5 shows 2-2Rv1 cells treated with indicated concentrations of Compound A for 3 days. Proliferation was measured both at Day 0 and at Day 3, and percent of growth was determined using Luciferase assay.

The current standard of care for prostate cancer comprises Androgen Depletion Therapy (ADT) but after a rapid remission, cancer cells eventually acquire resistance and Castration Resistant Prostate Cancer (CRPC) progresses. 22Rv.1 prostate cancer cells express the AR splice variant AR-V7 which mediates resistance to AR antagonist like Enzalutamide. This cell line was used as a model of CRPC. To test the role of BETi in CRPC, 22Rv.1 cells were treated with Compound A. BETi negatively affects proliferation of 22Rv.1 with an IC50=0.0017 (FIG. 5). FIG. 5 graphically shows the percent of 22RV.1 cell growth related to Day 0 and DMSO (Y axis) versus the amount of Compound A (X axis).

Figure 6:
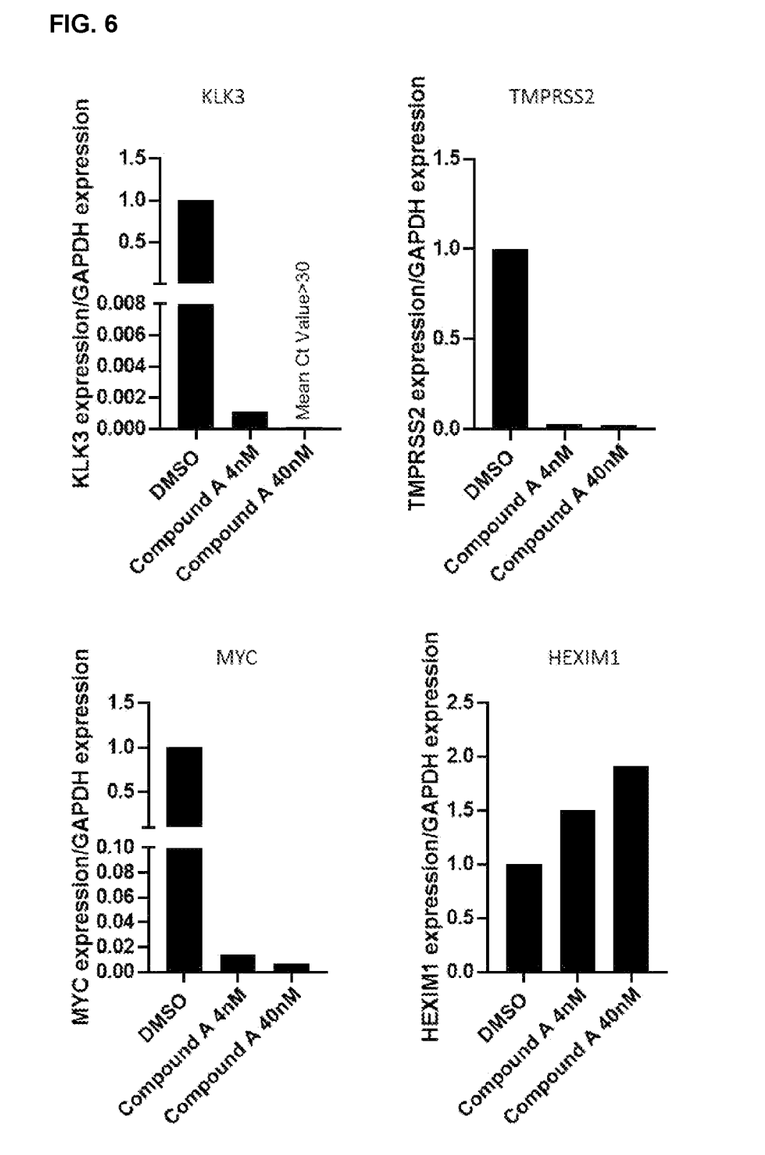
FIG. 6 shows 22Rv1 cells treated with indicated concentrations of Compound A for 48 hours. KLK3, TMPRSS2, MYC and HEXIM1 genes expression have been determined by qPCR.

To determine the effect of Compound A on AR target genes, 22Rv.1 cells were treated with two different concentrations of Compound A (4 nM and 40 nM). AR target genes were both strongly downregulated with 99.9% or 99.8% of downregulation observed for KLK3 when 4 nM or 40 nM of Compound A was added to the cells. A 97.0% or 97.8% of reduction compared to DMSO was measured for TMPRSS2 when cells were treated with 4 nM or 40 nM of Compound A respectively (FIG. 6 top). BET target gene MYC was downregulated with 98.5% downregulation when 4 nM of Compound A was added and 99.3% downregulation when cells were treated with 40 nM of Compound A. When cells were treated with 4 nM of Compound A 31% of induction of HEXIM1 was observed, while a 91.5% of upregulation was measured when cells were treated with 40 nM of Compound A (FIG. 6 bottom). Similarly, to what was observed for VCaP and LNCaP, cell proliferation of CRPC 22Rv.1 is impaired and AR signaling is mis-regulated in cells treated with BETi.

Figure 7:
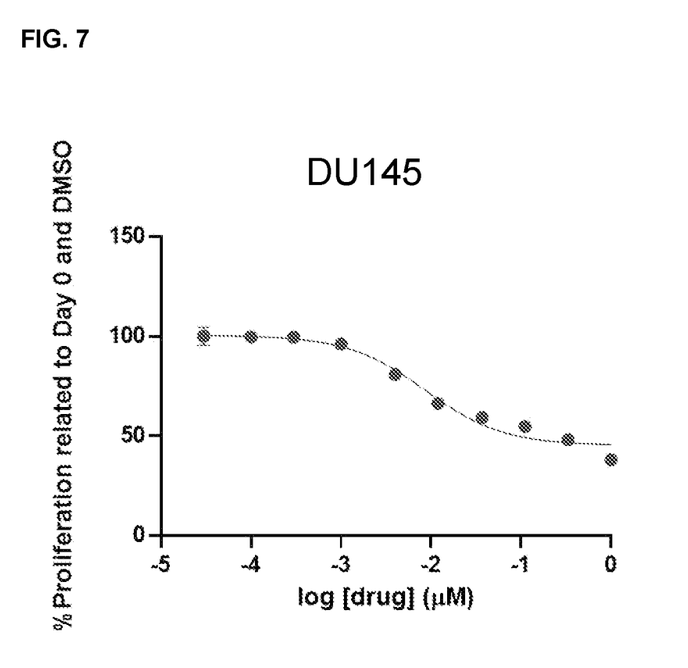
FIG. 7 shows DU145 cells treated with indicated concentrations of Compound A for 3 days. Proliferation was measured both at Day 0 and at Day 3, and percent of growth was determined using Luciferase assay.

A subset of CRPC patients develops an AR-independent disease characterized by a Neuroendocrine (NE) phenotype with low or absent AR expression. Mechanisms leading to drug resistance and to the development of a NE phenotype are still not completely understood. Prostate cancer cells DU145 are AR negative cell lines which do not respond to androgens. To test the effect of BETi in AR negative cells, DU145 have been treated with Compound A and a 61.9% reduction of DU145 proliferation was observed (FIG. 7). FIG. 7 visually show a graph of the percent of cell growth of DU145 cells related to Day 0 and DMSO (Y axis) versus the amount of Compound A (X axis).

Figure 8:
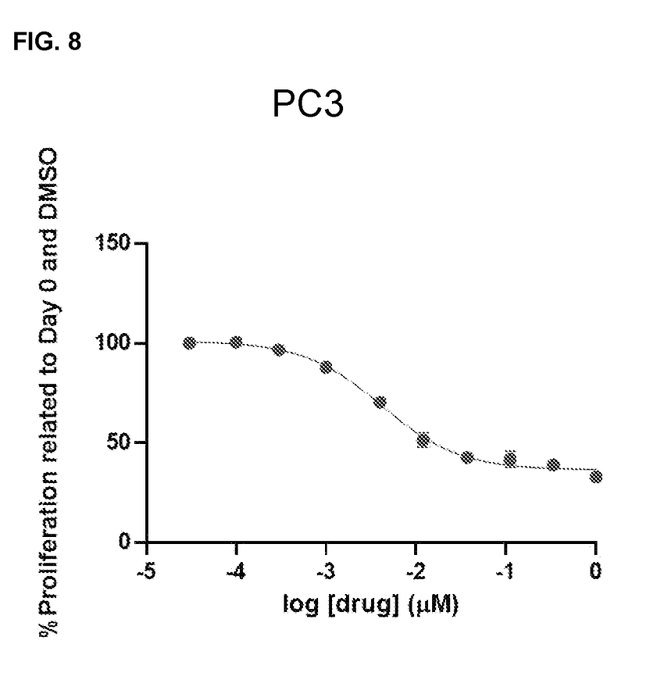
FIG. 8 shows PC3 cells treated with indicated concentrations of Compound A for 3 days. Proliferation was measured both at Day 0 and at Day 3, and percent of growth was determined using Luciferase assay.

Prostate cancer cells PC3 are a widely accepted NEPC cell model. To further corroborate the effect of BETi on NEPC, PC3 cells were treated with Compound A. Compound A showed 67% reduction of PC3 proliferation (IC$_{50}$ Compound A=0.0041) (FIG. 8). FIG. 8 visually show a graph of the percent of cell growth of PC3 cells related to Day 0 and DMSO (Y axis) versus the amount of Compound A (X axis).

These data show that BETi Compound A caused ≥61.9% reduction of cell proliferation in all Neuroendocrine prostate cancer models tested.

In summary the data show the ability of BETi Compound A to substantially and/or completely arrest cell proliferation and induce cell death in Prostate Carcinoma cells, and support the use of Compound A and structurally related compounds as a new and targeted therapy for solid tumors.

Tricyclic compounds useful as bromodomain inhibitors are disclosed in U.S. patent application Ser. No. 14/580,355 (U.S. Pat. No. 9,458,155).

In any of the embodiments described herein, Compound A is 2-[3-(1,4-dimethyl-1H-1,2,3-triazol-5-yl)-5-[(S)-(oxan-4-yl)(phenyl)methyl]-5H-pyrido[3,2-b]indol-7-yl]propan-2-ol, which has the following structure:

Compound A or the pharmaceutically acceptable salt thereof. The above compound has the chemical formula of $C_{30}H_{33}N_5O_2$ and a molecular weight of 495.62. The synthesis of this compound is disclosed in in U.S. patent application Ser. No. 14/580,355 (U.S. Pat. No. 9,458,155).

Pharmaceutically acceptable salts of include, but are not limited to, acid addition salts, formed by reacting the compound with a pharmaceutically acceptable inorganic acid, such as, for example acid addition salts, formed by reacting the compound with a pharmaceutically acceptable inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like.

II. Pharmaceutical Compositions

In any of the embodiments described herein, the bromodomain inhibitors described herein, or the pharmaceutically acceptable salts thereof, are formulated into pharmaceutical compositions.

Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. In some embodiments, a pharmaceutical composition disclosed herein comprises one or more pharmaceutically acceptable carriers, such as an aqueous carrier, buffer, and/or diluent.

Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules: as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. Suitable nontoxic solid carriers also include pharmaceutical grades of mannitol, lactose, starch, magnesium stearate, sodium saccharin, talcum, cellulose, glucose, sucrose, magnesium carbonate, and the like.

The compounds described herein may be combined or coordinately administered with a suitable carrier or vehicle depending on the route of administration. As used herein, the term "carrier" means a pharmaceutically acceptable solid or liquid filler, diluent or encapsulating material. A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention.

The pharmaceutical composition comprising the compounds described herein, or the salts thereof, will be formulated and dosed in a fashion consistent with good medical practice, taking into account the clinical condition of the individual patient, the method of administration, the scheduling of administration, and other factors known to practitioners.

III. Methods of Treatment

The present application provides methods of treating prostate cancer using any one of the bromodomain inhibitors described herein, or pharmaceutically acceptable salts thereof.

In any of the embodiments described herein, a therapeutically effective amount of the bromodomain inhibitor can be used. In some embodiments, the therapeutically effective amount of the bromodomain inhibitor, or a pharmaceutically acceptable salt thereof, is in an amount to substantially induce cell cycle arrest of the prostate cancer cell. In some embodiments, the therapeutically effective amount of the bromodomain 1 inhibitor, or a pharmaceutically acceptable salt thereof, is in an amount to completely induce cell cycle arrest of prostate cancer cell. In some embodiments, the therapeutically effective amount of the bromodomain inhibitor, or a pharmaceutically acceptable salt thereof, is in an amount to induce apoptosis of androgen independent cancer cells.

In one aspect of the methods described herein, the methods result in substantially inducing cell cycle arrest of prostate cancer cell, wherein "substantially" is defined as at least about 50%, at least about 55%, at least about 60%, at least about 65%, at least about 70%, at least about 75%, at least about 80%, at least about 85%, at least about 90%, at least about 95%, or at least about 100% cell cycle arrest of the prostate cancer cell. The percent cell cycle arrest of the prostate cancer cells can be measured using any clinically acceptable technique.

In another aspect of the methods described herein, the methods result in completely inducing cell cycle arrest of the prostate cancer cells. The cell cycle arrest of the prostate cancer cells can be measured using any clinically acceptable technique.

Finally, in another aspect of the methods described herein, the methods result in inducing apoptosis of androgen independent cancer cells. For example, the methods can result in inducing about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100% apoptosis of androgen independent cancer cells. Apopotosis of the androgen independent cancer cells can be measured using any clinically acceptable technique.

Provided in one aspect is a method of treating prostate cancer in a subject in need thereof comprising administering to the subject a composition comprising bromodomain inhibitor, or a pharmaceutically acceptable salt thereof.

In any of the embodiments described herein, the prostate cancer can be castration resistant prostate cancer (CPRC), neuroendocrine prostate cancer (NEPC), anti-androgen resistant prostate cancer, or any combination thereof. In some embodiments, the prostate cancer is castration resistant prostate cancer (CPRC). In some embodiments, the prostate cancer is neuroendocrine prostate cancer (NEPC). In some embodiments, the prostate cancer is anti-androgen resistant prostate cancer.

In any of the embodiments described herein, the prostate cancer to be treated can be in an advanced stage. In any of the embodiments described herein, the prostate cancer can be metastatic. In any of the embodiments described herein, the prostate cancer to be treated can have metastasized to regions of the patient's body other than the prostate gland. In any of the embodiments described herein, the prostate cancer to be treated can have re-occurred in the patient following a significant period of remission.

In any of the embodiments described herein, the method can result in (a) at least about 40% reduction of cancer cell proliferation; (b) from about 40% to about 99% reduction of cancer cell proliferation; and/or (c) in about 20%, about 25%, about 30%, about 35%, about 40%, about 45%, about 50%, about 55%, about 60%, about 65%, about 70%, about 75%, about 80%, about 85%, about 90%, about 95%, or about 99% reduction of cancer cell proliferation. In some embodiments, the method results in at least about 40% reduction of cancer cell proliferation. In some embodiments, the method results in from about 40% to about 99% reduction of cancer cell proliferation. In some embodiments, the method results in about 20%, about 25%, about 30%, about 35%, about 40%, about 45%, about 50%, about 55%, about 60%, about 65%, about 70%, about 75%, about 80%, about 85%, about 90%, about 95%, or about 99% reduction of cancer cell proliferation.

In any of the embodiments described herein, the method results in (a) at least about 40% reduction of tumor size; (b) from about 40% to about 99% reduction of tumor size; and/or (c) about 20%, about 25%, about 30%, about 35%, about 40%, about 45%, about 50%, about 55%, about 60%, about 65%, about 70%, about 75%, about 80%, about 85%, about 90%, about 95%, or about 99% reduction of tumor size. In some embodiments, the method results in at least about 40% reduction of tumor size. In some embodiments, the method results in from about 40% to about 99% reduction of tumor size. In some embodiments, the method results in about 20%, about 25%, about 30%, about 35%, about 40%, about 45%, about 50%, about 55%, about 60%, about 65%, about 70%, about 75%, about 80%, about 85%, about 90%, about 95%, or about 99% reduction of tumor size.

A. Routes of Administration

Administration may be via any route of administration. Non-limiting examples include nasal, sublingual, buccal, rectal, intravenous, intra-arterial, intradermal, intraperitoneal, intrathecal, intramuscular, epidural, intracerebral, intracerebroventricular, transdermal, or any combination thereof.

The compounds or pharmaceutical compositions described herein are administered in a manner appropriate to the disease to be treated and/or prevented. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In any of the embodiments described herein, the bromodomain inhibitor, or a pharmaceutical acceptable salt thereof, is adapted for oral administration. Suitable forms for oral administration include, but are not limited to, a tablet, pill, sachet, or capsule of hard of soft gelatin.

B. Kits

The compounds or compositions described herein of the invention may be packaged together with, or included in a kit along with instructions or a package insert. Such instructions or package inserts may address recommended storage conditions, such as time, temperature and light, taking into account the shelf-life of the bromodomain inhibitor or the salts thereof. Such instructions or package inserts may also address the particular advantages of the compounds described herein or derivatives or salts thereof, such as the ease of storage for formulations that may require use in the field, outside of controlled hospital, clinic or office conditions.

The invention also provides a pharmaceutical pack or kit comprising one or more containers filled with one or more pharmaceutical compositions disclosed herein. The kits may include, for instance, containers filled with an appropriate amount of a pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the bromodomain inhibitor or the salts thereof may be employed in conjunction with other therapeutic compounds.

In one aspect, the kit may comprise one or more devices, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

In one aspect, the kit may comprise a device, and may further comprise instructions for use. In one aspect, the instructions may comprise visual aid/pictorial and/or written directions to an administrator of the device.

IV. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/of" refers to and encompasses any and all possible combinations of one or more of the listed items, as well as the lack of combinations when interpreted in the alternative ("or").

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "administering" as used herein includes prescribing for administration as well as actually administering, and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., *Pharmaceutical Salts*, J. Pharma. Sci. 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

EXAMPLES

As used in the following examples, Compound A refers to is 2-[3-(1,4-dimethyl-1H-1,2,3-triazol-5-yl)-5-[(S)-(oxan-4-yl)(phenyl)methyl]-5H-pyrido[3,2-b]indol-7-yl]propan-2-ol.

The below list identifies abbreviations used in the following examples.

| Abbreviation | Full Name |
|---|---|
| BET | Bromo and Extra-Terminal domain |
| PSA | Prostate-Specific Antigen |
| AR | Androgen receptor |
| BETi | BET inhibitors |

| Abbreviation | Full Name |
|---|---|
| KLK3 | Kallikrein Related Peptidase 3 |
| TPRSS2 | Transmembrane Serine Protease 2 |
| HEXIM1 | Hexamethylene Bis-Acetamide-Inducible Protein 1 |
| ADT | Androgen Depletion Therapy |
| CRPC | Castration Resistant Prostate Cancer |
| NE | Neuroendocrine |
| NEPC | Neuroendocrine prostate cancer |

Example 1

The following example evaluates the ability of BETi Compound A to completely arrest cell proliferation and induce cell death in prostate carcinoma and neuroendocrine prostate cancer cells.

Materials and Methods
Cell Culture

VCaP, LNCaP, 22Rv.1, DU145 and PC3 cancer cell lines were obtained from ATCC. VCaP were cultured in DMEM media supplemented with 8% FBS, LNCaP, 22Rv.1 and DU145 were cultured in RPMI1640 media supplemented with 10% FBS, and PC3 were cultured in F12K media supplemented with 10% FBS.

Proliferation Assay

Cells were plated in a 96-well format and were allowed to adhere 24 h before treatment. Drugs were titrated 1:3 from 1 µM to 0.1 nM with 9 doses in triplicate. Cell proliferation was measured on the day of treatment (Day 0) and on Day 3 using Cell Titer-Glo reagent (Promega) according to the manufacturer's instructions. Cell growth normalized to the DMSO vehicle control and to Day 0 was fitted by nonlinear regression using GraphPad Prism 7.03 (GraphPad Software, Inc.).

Gene Expression Analysis

Cells were plated in a 6-well format and were allowed to adhere 24 h before treatment. Cells were treated for 48 h before collecting them. RNA was purified from cells using the RNeasy kit (Qiagen) according to the manufacturer's instructions. Quantitative RTPCR was performed using the TaqMan assay (Thermo Fisher Scientific) on the ABI Quant-Studio 7 Flex Real-Time PCR System.

Results
Compound a Causes a Complete Growth Arrest and Induces Cell Death of Prostate Carcinoma Cells.

VCaP cells exhibit characteristics of clinical prostate carcinoma including expression of Prostate-Specific Antigen (PSA) and androgen receptor (AR), and are used as a model to study prostate cancer progression and metastasis. To test the role of Bromo and Extra-Terminal domain (BET) inhibition in prostate cancer VCaP cells have been treated with BET inhibitor (BETi) Compound A. Compound A affects VCaP proliferation causing a complete (100%) growth arrest at 0.1 uM. Moreover, at the highest concentrations Compound A exhibits cytotoxic effect (FIG. 1).

BET proteins regulate AR signaling through modulation of AR target genes. To test if BETi modulates AR target genes VCaP cells have been treated with Compound A and gene expression was measured. Two AR target genes Kallikrein Related Peptidase 3 (KLK3) and Transmembrane Serine Protease 2 (TMPRSS2) are both downregulated after treatment with Compound A. When cells were treated with 4 nM Compound A, 96.9% of downregulation of KLK3 was observed, while 99.4% downregulation was measured when cells were treated with 40 nM of Compound A (FIG. 2 top). A downregulation was also observed for TMPRSS2 with 32.8% and 51.9% of downregulation when 4 nM or 40 nM of Compound A were respectively administered to cells (FIG. 2 top). BET target genes such as MYC and Hexamethylene Bis-Acetamide-Inducible Protein 1 (HEXIM1) were also modulated by Compound A. In cells treated with 4 nM of Compound A 91.4% of reduction in MYC expression was observed, while in cells treated with 40 nM of Compound A 95.7% of MYC downregulation was measured. HEXIM1 was 968.0% and 1257.5% upregulated compared to DMSO when either 4 nM or 40 nM of Compound A was administered to VCaP cells (FIG. 2 bottom).

To further corroborate a role of BETi in prostate cancer LNCaP cells established from a metastatic lesion of human prostatic adenocarcinoma have been treated with Compound A. Treatment with Compound A causes a complete (100%) growth arrest at 1 uM (FIG. 3).

AR signaling was monitored in LNCaP cells after treatment with Compound A and downregulation of KLK3 was observed with 58.8% and 92.0% of downregulation when 4 nM or 40 nM were respectively administered to the cells (FIG. 4). BETi target genes were also modulated. A downregulation of 84.1% of MYC was observed when 4 nM of Compound A was administered to the cells and 93.6% of downregulation was measured when 40 nM of Compound A was given to LNCaP cells. Finally, an upregulation of 446.8% and 533.3% of HEXIM1 was measured when cells were treated with respectively 4 nM and 40 nM of Compound A (FIG. 4)

Compound a Impairs Proliferation of Castration Resistant Prostate Cancer Cells.

Current standard of care for prostate cancer consists in Androgen Depletion Therapy (ADT) but after a rapid remission cancer cells eventually acquire resistance and Castration Resistant Prostate Cancer (CRPC) progresses.

22Rv.1 prostate cancer cells express the AR splice variant AR-V7 which mediates resistance to AR antagonist like Enzalutamide. This cell line has been used as a model of CRPC. To test the role of BETi in CRPC, 22Rv.1 cells were treated with Compound A. BETi negatively affects proliferation of 22Rv.1 with an IC50=0.0017 (FIG. 5).

To determine the effect of Compound A on AR target genes, 22Rv.1 cells were treated with two different concentrations of Compound A (4 nM and 40 nM). AR target genes were both strongly downregulated with 99.9% or 99.8% of downregulation observed for KLK3 when 4 nM or 40 nM of Compound A was added to the cells. A 97.0% or 97.8% of reduction compared to DMSO was measured for TMPRSS2 when cells were treated with 4 nM or 40 nM of Compound A respectively (FIG. 6 top). BET target gene MYC was downregulated with 98.5% downregulation when 4 nM of Compound A was added and 99.3% downregulation when cell were treated with 40 nM of Compound A. HEXIM1 was upregulated and 31% of induction was observed when cells were treated with 4 nM of Compound A, while a 91.5% of upregulation was measured when cells were treated with 40 nM of Compound A (FIG. 6 bottom).

Similarly, to what was observed for VCaP and LNCaP, cell proliferation of CRPC 22Rv.1 is impaired and AR signaling is mis-regulated in cells treated with BETi.

Compound A Strongly Reduces Proliferation of Neuroendocrine Prostate Cancer Cells.

A subset of CRPC patients develops an AR-independent disease characterized by a Neuroendocrine (NE) phenotype with low or absent AR expression.

Prostate cancer cells DU145 are AR negative cell lines which do not respond to androgens. To test the effect of BETi in AR negative cells, DU145 were treated with Compound A and a 61.9% reduction of DU145 proliferation was observed (FIG. 7).

Prostate cancer cells PC3 are another AR negative cell line widely accepted as NEPC cell model. To test the effect of BETi on NEPC, PC3 cells were treated with Compound A. Compound A shows 67% reduction of PC3 proliferation with an IC50=0.0041 (FIG. 8).

In summary, our data show the ability of Compound A to arrest cell proliferation and affect AR signaling of prostate carcinoma cells supporting its potential as a new and targeted therapy for these solid tumors.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims

What is claimed is:

1. A method of treating prostate cancer in a subject in need thereof comprising administering to the subject a therapeutically effective amount of Compound A having the structure, Compound A or a pharmaceutically acceptable salt thereof, and wherein the prostate cancer is castration resistant prostate cancer (CPRC), neuroendocrine prostate cancer (NEPC), anti-androgen resistant prostate cancer, or any combination thereof.

2. The method of claim 1, wherein the prostate cancer is metastatic.

3. The method of claim 1, wherein the prostate cancer to be treated is in an advanced stage.

4. The method of claim 1, wherein the prostate cancer to be treated has metastasized to regions of the subject's body other than the prostate gland.

5. The method of claim 1, wherein the prostate cancer to be treated has re-occurred in the subject following a significant period of remission.

6. The method of claim 1, wherein the prostate cancer is castration resistant prostate cancer (CPRC).

7. The method of claim 6, wherein the castration resistant prostate cancer (CPRC) is an androgen receptor (AR) independent disease characterized by neuroendocrine phenotype with a low or absent AR expression.

8. The method of claim 1, wherein the prostate cancer is neuroendocrine prostate cancer (NEPC).

9. The method of claim 1, wherein the method results in substantially inducing cell cycle arrest of the prostate cancer.

10. The method of claim 9, wherein "substantially" is defined as at least about 50% cell cycle arrest of the prostate cancer.

11. The method of claim 1, wherein the method results in completely inducing cell cycle arrest of the prostate cancer.

12. The method of claim 1, wherein the method induces apoptosis of androgen independent cancer cells.

13. The method of claim 12, wherein the method results in inducing about 20% or more apoptosis of the androgen independent cancer cells.

14. The method of claim 1, wherein:
the method results in from about 70% to about 99% reduction of cancer cell proliferation.

15. The method of claim 1, wherein:
the method results in from about 40% to about 99% reduction of tumor size.

16. The method of claim 1, wherein the compound, or a pharmaceutically acceptable salt thereof, is adapted for oral administration.

17. The method of claim 16, wherein the compound, or a pharmaceutically acceptable salt thereof, is in the form of a tablet, pill, sachet, or capsule of hard of soft gelatin.

* * * * *